US011467147B2

(12) United States Patent
Lascaux

(10) Patent No.: US 11,467,147 B2
(45) Date of Patent: Oct. 11, 2022

(54) METHOD FOR MAPPING THE CONCENTRATION OF AN ANALYTE IN AN ENVIRONMENT

(71) Applicant: ELICHENS, Grenoble (FR)

(72) Inventor: Franck Lascaux, La Verpillière (FR)

(73) Assignee: ELICHENS, Grenoble (FR)

( * ) Notice: Subject to any disclaimer, the term of this patent is extended or adjusted under 35 U.S.C. 154(b) by 458 days.

(21) Appl. No.: 16/499,179

(22) PCT Filed: Mar. 27, 2018

(86) PCT No.: PCT/FR2018/050741
§ 371 (c)(1),
(2) Date: Sep. 27, 2019

(87) PCT Pub. No.: WO2018/178561
PCT Pub. Date: Oct. 4, 2018

(65) Prior Publication Data
US 2020/0025738 A1 Jan. 23, 2020

(30) Foreign Application Priority Data
Mar. 29, 2017 (FR) ........................................ 1752654

(51) Int. Cl.
*G01N 33/00* (2006.01)
*G01N 27/327* (2006.01)
(Continued)

(52) U.S. Cl.
CPC ..... *G01N 33/0075* (2013.01); *G01N 27/3274* (2013.01); *G01N 33/0031* (2013.01); *G06F 17/11* (2013.01); *G06F 17/16* (2013.01)

(58) Field of Classification Search
CPC ............... G01N 33/00; G01N 33/0075; G01N 27/3274; G01N 33/0031;
(Continued)

(56) References Cited

U.S. PATENT DOCUMENTS 5,798,768 A * 8/1998 Cacas .................... G06T 17/05
345/441
8,949,037 B2 * 2/2015 Prince ................ G01N 33/0027
73/1.06
(Continued)

FOREIGN PATENT DOCUMENTS

CN 103258116 A 8/2013
CN 105373673 A 3/2016

OTHER PUBLICATIONS

Kennedy Werea in A comparative assessment of support vector regression, artificial neural networks,and random forests for predicting and mapping soil organic carbon stocks across an Afromontane landscape, Ecological Indicators52(2015)394-403 (Year: 2015).*
(Continued)

*Primary Examiner* — Tung S Lau
(74) *Attorney, Agent, or Firm* — TraskBritt

(57) ABSTRACT

A method for estimating a mapping of the concentration of an analyte in an environment uses sensors distributed in the environment. Each sensor generates a measurement of the analyte concentration at various measurement instants, which measurements are carried out by each sensor at each measurement instant, forming an observation vector, each term of which corresponds to a measurement arising from a sensor. The environment is spatially meshed with a plurality of mesh cells. The analyte concentration at each mesh cell, at each measurement instant, forms a "state vector," each term of which corresponds to an analyte concentration in a mesh cell. A "global bias" is determined and used to correct the state vector to obtain a "debiased state vector." The state vector is also corrected by a local correction vector as a function of a correction vector.

15 Claims, 3 Drawing Sheets

(51) Int. Cl.
  *G06F 17/11*     (2006.01)
  *G06F 17/16*     (2006.01)
(58) Field of Classification Search
  CPC ........ G01N 2033/0068; G01N 33/0004; G06F 17/11; G06F 17/16; G06F 17/10
  See application file for complete search history.

(56) References Cited

U.S. PATENT DOCUMENTS

| | | | | |
|---|---|---|---|---|
| 10,788,836 | B2* | 9/2020 | Ebrahimi Afrouzi | .......................... G05D 1/0246 |
| 11,125,619 | B2* | 9/2021 | Murphy | ................. G01J 3/0237 |
| 11,241,791 | B1* | 2/2022 | Ebrahimi Afrouzi | ... G06T 7/262 |
| 11,274,929 | B1* | 3/2022 | Afrouzi | ................ G05D 1/0272 |
| 2008/0195329 | A1* | 8/2008 | Prince | ................ G01N 33/0027 702/23 |
| 2013/0138349 | A1* | 5/2013 | Kram | ....................... G01V 9/02 702/12 |
| 2013/0179078 | A1* | 7/2013 | Griffon | ................... G01W 1/10 702/3 |
| 2013/0249909 | A1* | 9/2013 | Thompson | .............. G06T 17/05 345/420 |
| 2017/0255720 | A1* | 9/2017 | Satoh | .................... G06F 17/175 |
| 2018/0180415 | A1* | 6/2018 | Gallant | .................... G01V 7/06 |

OTHER PUBLICATIONS

International Search Report and International Written Opinion for International Application PCT/FR2018/050741, dated Jul. 5, 2018, 15 pages (not including translation).

Silver Jeremy David et al, Dynamic parameter estimation for a street canyon air quality model, Environmental Modelling & Software, vol. 47, Jun. 25, 2013, pp. 235-252.

Costa Marco et al, Bias-correction of Kalman filter estimators associated to a linear state space model with estimated parameters, Journal of Statistical Planning and Inference, vol. 176, Apr. 19, 2016, pp. 22-32.

Ottosen Thor-Bjorn et al., A parameter estimation and identifiably analysis methodology applied to a street canyon air pollution model, Environmental Modelling & Software, Elsevier, Amsterdam, NL, vol. 84, Jul. 12, 2016, pp. 165-176.

Wenjun LV et al., Fusion approach for real-time mapping street atmospheric pollution concentration, 2016 9th International Conference on Human System Interactions (HSI), IEE Jul. 6, 2016, pp. 133-139.

European Communication pursuant to Article 94(3) EPC for European Application No. 18722647, dated Dec. 2, 2021, 18 pages with English translation.

* cited by examiner

METHOD FOR MAPPING THE CONCENTRATION OF AN ANALYTE IN AN ENVIRONMENT

CROSS-REFERENCE TO RELATED APPLICATIONS

This application is a national phase entry under 35 U.S.C. § 371 of International Patent Application PCT/FR2018/050741, filed Mar. 27, 2018, designating the United States of America and published in French as International Patent Publication WO 2018/178561 A1 on Oct. 4, 2018, which claims the benefit under Article 8 of the Patent Cooperation Treaty to French Patent Application Serial No. 1752654, filed Mar. 29, 2017.

TECHNICAL FIELD

The technical field of the disclosure is the mapping of analytes in the environment, and more particularly a mapping of polluting molecules or of noxious particles that are harmful to the environment.

BACKGROUND

The obtaining of mappings describing the spatial distribution of concentrations of noxious molecules or particles is a need that addresses an expectation of the population and the authorities, in particular, in urban areas. Numerous models have been developed making it possible to establish mappings of atmospheric pollution and to forecast their temporal evolutions. It is then possible to model the pollution of the air in an urban setting in a routine situation, or in an accidental situation, for example, following a chemical or nuclear accident. The geographical coverage may be limited to a few $km^2$, or indeed to the scale of a country or continent in applications aimed at modelling the large-scale transport of pollutants. On the basis of data relating to sources of pollutant emissions, and by considering parameters linked with topographical or meteorological conditions, the models make it possible to establish the spatial distribution of concentrations of polluting molecules or particles in the environment, the latter forming the subject of a spatial meshing.

The publication Berkowicz R. "Modelling traffic pollution in streets", January 1997, from the National Environmental Research Institute, a Danish organization, describes, for example, a model of spatial dispersion of pollutants adapted to the specifics of urban settings. Indeed, in an urban setting, the particular topography formed of streets separated by buildings justifies a specific approach, taking account of the formation of air circulation vortices at street level, these vortices playing a determining role in the dispersion of atmospheric pollution. Such models are referred to by the terms "Street Canyon Model" or "Street Model". The aforementioned publication describes a model for estimating pollution in an urban setting referred to by the acronym OSPM, standing for "Operational Street Pollution Model", or equivalently, operational urban pollution model. According to this model, on the basis of the emission of a pollutant in a street, depending on the number of vehicles and an average emission per vehicle, the model takes into account the recirculation vortex formed in the street, the aerological turbulence resulting from road traffic, the ambient pollution, originating from other streets, as well as the wind circulating at canopy level, that is to say above the urban setting. The publication Berkowicz R. "OSPM, a parameterised street pollution model", Environmental Monitoring and Assessment 65:323-331, 2000," also presents the assumptions on which the OSPM model is based, as well as an experimental validation of this model. The publication Silver J. D. "Dynamic parameter estimation for a street canyon air quality model", Environmental Modelling & Software, vol. 47, 2013-06-25, describes a method, implementing a Kalman filter, for obtaining the parameters of a model of OSPM type.

Certain models can be affected by a bias. The publication Costa M. "Bias-correction of Kalman filter estimators associated to a linear state space model with estimated parameters", Journal of Statistical Planning and inference 176 (2016) 22-32, tackles this problem by implementing a Kalman filter, each iteration of which comprises an estimation of a bias. The question of the bias affecting a model is also dealt with in CN105373673.

Pollution models can be fitted against measurements carried out locally, these measurements allowing an adjustment; fitting measured observations against a theoretical model is referred to by the term "data assimilation". A data assimilation technique is, for example, described in the publication Nguyen C. "Evaluation of Data assimilation Method at the Urban Scale With the Sirane Model". The publication describes tailoring a model of nitrogen dioxide dispersion in an urban setting by taking into account measurements performed by 16 measurement stations distributed in a city. A similar technique is described in the publication Tilloy A. "Blue-based NO2 data assimilation at urban scale", Journal of Geophysical research: Atmospheres, Vol 118, 2031-2040.

This disclosure is aimed at enhancing the schemes set out in the publications, in such a way as to improve the fit between the models and measurements performed by sensors distributed in the modelled environment.

BRIEF SUMMARY

A subject of the present disclosure is a method for estimating a mapping of the concentration of an analyte in an environment, on the basis of sensors distributed in the environment,
- each sensor generating a measurement of the analyte concentration at various measurement instants, the measurements carried out by each sensor at each measurement instant forming an observation vector, each term of which corresponds to a measurement arising from a sensor;
- the environment forming the subject of a spatial meshing defining a plurality of mesh cells, the concentration or the quantity of the analyte at the level of each mesh cell, at each measurement instant, forming a vector, the so-called state vector, each term of which corresponds to a concentration or to a quantity of analyte in a mesh cell;

the method comprising the following steps:
- a) on the basis of the measurements performed by each sensor, obtaining of a, so-called measured, observation vector at a measurement instant;
- b) obtaining of a state vector at the measurement instant and, on the basis of the state vector, estimation of an observation vector at the measurement instant;
- c) comparison of the estimation, obtained in step b), of the observation vector with the measured observation vector resulting from step a), and, on the basis of the comparison, determination of a global bias at the measurement instant, the global bias being a scalar representative of the comparison between several terms respectively of the estimated observation vector and of the measured observation vector;

d) correction of the state vector arising from step b) as a function of the global bias obtained during step c), so as to obtain a so-called debiased state vector at the measurement instant;

e) on the basis of the debiased state vector obtained during step d), debiased estimation of the observation vector at the measurement instant;

f) comparison of the debiased estimation of the observation vector resulting from step e) with the measured observation vector resulting from step a), and, on the basis of the comparison, determination of a local correction vector; and g) updating of the state vector at the measurement instant, the latter being replaced with a sum of the debiased state vector resulting from step d) with the local correction vector resulting from step f), the updating of the state vector making it possible to estimate the mapping of the concentration of the analyte in various mesh cells of the environment.

The global bias determined during step c) is preferably a scalar, the latter being subtracted from each term of the state vector during step d). Step d) is therefore a global correction step.

The analyte can be a molecule or a particle, dispersed in a gas. It is generally an analyte considered to be harmful to the environment or the population. The environment can be a geographical area, such as an urban area, the air of which may be affected by pollution.

The local correction vector is a vector whose terms may differ from one another, and are so quite generally. At least two terms of the local correction vector differ from one another. Step g) is therefore a local correction step, the state vector being updated as a function of local variations of the analyte concentration.

The method can comprise one of the following characteristics, taken in isolation or in combination:

during step b), the observation vector is estimated by applying a matrix, the so-called observation operator, to the state vector. This matrix makes it possible to interpolate the values of the state vector at each position respectively occupied by the various sensors. Each term of the state vector is associated with a mesh cell and with a sensor, the term being all the higher the closer the mesh cell is to the sensor.

Step c), comprises the following sub-steps:
ci) establishment of comparisons, for example, in the form of a subtraction or of a ratio, between various terms of the observation vector estimated during step b) and of the observation vector measured during step a);
cii) calculation of an average or median value of each comparison resulting from sub-step ci); and
ciii) obtaining of the global bias on the basis of the average or median value resulting from sub-step cii).

Step d) comprises a subtraction of the global bias from various terms, and preferably from each term, of the state vector.

During step e), the debiased estimation of the observation vector is obtained by applying a matrix, the so-called observation operator, to the debiased state vector.

During step f), the correction vector is determined according to the following sub-steps:
fi) establishment of a comparison vector, resulting from a comparison, term by term, in the form of a subtraction or of a ratio, between the observation vector resulting from step a) and the debiased estimation of the observation vector resulting from step e);
fii) taking into account of a gain matrix, each term of which is associated with a mesh cell and with a sensor, the term being all the higher the closer the mesh cell is to the sensor; and
fiii) application of the gain matrix to the comparison vector so as to form a correction vector.

Subsequent to step g), the method comprises a step h) of iterative updating of the state vector, with each iteration there being associated an iteration rank, step h) comprising the following sub-steps:
hi) taking into account of a gain matrix corresponding to the rank of the iteration;
hii) determination of a comparison vector, associated with the rank of the iteration, by comparing the observation vector resulting from step a) with a vector resulting from the application of a matrix, the so-called observation operator, to the state vector resulting from step g), or resulting from a previous iteration;
hiii) application of the gain matrix taken into account during sub-step hi) to the comparison vector determined during sub-step hii), in such a way as to obtain a local correction vector associated with the rank of the iteration;
hiv) updating of the state vector, the latter being replaced with a sum of the state vector resulting from step g), or from a previous iteration, with the local correction vector resulting from sub-step hiii); and
hv) repetition of sub-steps hi) to hiv) or stopping of the iteration.

During step h), in the course of each iteration, to each sensor can be allotted a neighbourhood extending according to a maximum distance, the terms of the gain matrix that are associated with the sensor being non-zero for the mesh cells situated inside the neighbourhood, the terms of the gain matrix that are associated with the mesh cells situated outside the neighbourhood being zero or less than the terms of the gain matrix that are associated with the mesh cells inside the neighbourhood.

Each term of the gain matrix is associated with a mesh cell and with a sensor, the value of the term being all the higher the closer the mesh cell is to the sensor.

Each term of the observation operator is associated with a mesh cell and with a sensor, the value of the term being all the higher the closer the mesh cell is to the sensor.

During step b), the state vector is formed by using a model established on the basis of data relating to the road traffic in the environment, of the topography of the environment as well as of meteorological data relating to the environment, the model resulting in an analyte concentration at the level of each mesh cell. It is, in particular, a model of OSPM type described in the publications cited with regard to the prior art.

According to one embodiment, the method comprises the following steps:
taking into account of a, so-called later, state vector at a later instant following the measurement instant; and
establishment of a correction of the later state vector as a function of the state vector updated, at the measurement instant, during step g) or during step h).

The correction can consist in the addition, to the later state vector, of a difference between the updated state vector and the state vector at the measurement instant.

Other advantages and characteristics will emerge more clearly from the following descriptions of particular embodiments of the disclosure, which descriptions are given by way of non-limiting examples and represented in the figures listed hereinbelow.

DETAILED DESCRIPTION

Figure 1A:
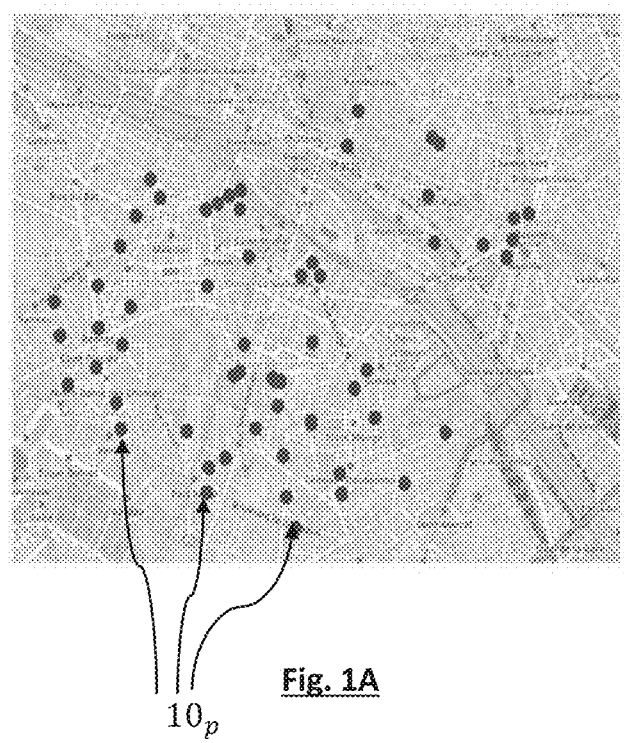
FIG. 1A is the plan of an urban area under study, within which measurement sensors are distributed.
Figure 1B:
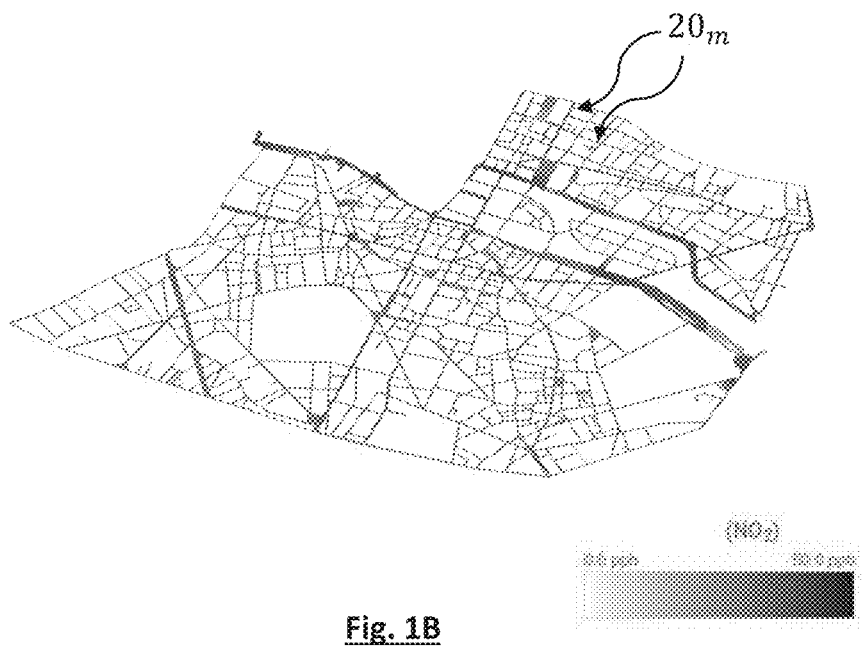
FIG. 1B is a mapping of an analyte, in this instance nitrogen dioxide, this mapping being obtained by application of a model of OSPM type.

FIG. 1A represents a plan of an urban area in which a two-dimensional mapping of the concentration of an analyte is modelled according to a model known from the prior art, for example, the OSPM model mentioned previously. In this example, the analyte is a nitrogen dioxide molecule. In general, the analyte is a chemical molecule or a particle whose dispersion in the environment one wishes to know, that is to say a spatial distribution of its concentration or of its quantity. It may, in particular, be an analyte arising from road traffic. FIG. 1B represents a mapping of nitrogen dioxide in the streets of the urban area represented in FIG. 1A. In FIG. 1B, the grey levels correspond to a nitrogen dioxide concentration expressed in ppb.

On the basis of the mapping modelled in FIG. 1B, it is possible to define a geographical meshing of the urban area, and to form, on the basis of the model, a vector, the so-called state vector M(t), each term $M_m(t)$ of which corresponds to a nitrogen dioxide concentration modelled at the level of a mesh cell $20_m$ at an instant t, for example, at the level of each mesh cell centre. The index m is a strictly positive integer designating a mesh cell. The dimension of the state vector M(t) is $(N_m, 1)$, where $N_m$ represents the number of mesh cells considered. Each term of the state vector is obtained by the application of a predictive model, such as the OSPM model described with regard to the prior art, by taking into account data linked with the urban traffic, meteorological parameters, such as the temperature and/or the speed of the winds, as well as the three-dimensional topography of the environment, for example, the geometry of the streets as well as the height of the buildings between each street.

Represented in FIG. 1A, in the form of dots, are simulated locations of sensors ($10_p$), the index p being a strictly positive integer designating a sensor. In the example represented, each sensor is a nitrogen dioxide sensor, measuring a concentration $c_p(t)$ of this analyte at each measurement instant t. The measured concentrations $c_p(t)$ form a vector C(t), the so-called observation vector, at the measurement instant, each term of which is a concentration measured by a sensor at the measurement instant. The dimension of the vector C(t) is $(N_p, 1)$, where $N_p$ represents the number of sensors considered. The sensors are connected to a processor, for example, a microprocessor, the latter being programmed to execute instructions to implement the method described in this disclosure.

Figure 2:
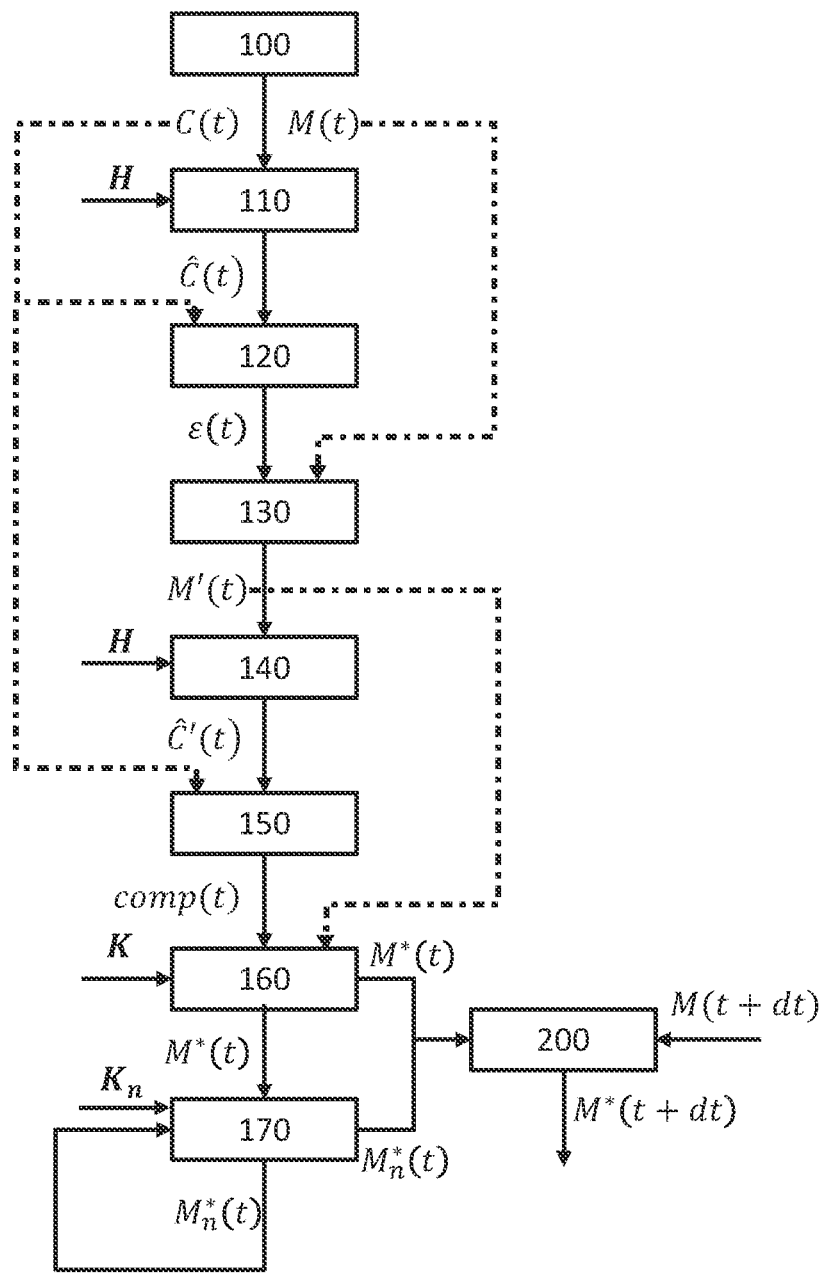
FIG. 2 shows the main steps of a method according to the disclosure.

On the basis of the state vector M(t) and of the observation vector C(t), the method described hereinbelow is aimed at updating the state vector, in such a way as to increase the precision of the mapping of the urban area considered, by taking into account the measurements performed by each sensor. Indeed, certain local features, not taken into account by the model, may have a local influence on the distribution of the analyte. This may, in particular, entail a bottleneck. This disclosure makes it possible to take them into account. The main steps of the method are represented in FIG. 2.

Preferably, the distance between two adjacent sensors is less than 500 m, or indeed than 200 m. Indeed, the method described hereinbelow is all the more effective the higher the number of sensors. In terms of number of sensors per unit area, preferably, the number of sensors is greater than 2 or indeed 3 per km². On the scale of a city, recourse to about ten or about twenty sensors is not sufficient to perform a sufficiently effective updating of the mapping.

Step 100: acquisition of the data.

This entails obtaining the state vector M(t) on the basis of the modelled mapping and of the observation vector C(t) on the basis of the sensors. FIG. 1B corresponds to a two-dimensional representation of the state vector M(t), which representation is obtained by establishing a correspondence between each term of this vector and a two-dimensional spatial coordinate $M_m(t)$ corresponding to a mesh cell $20_m$. In this example, the observation vector C(t) is obtained by simulation on the basis of concentrations established, at the level of each sensor $10_p$, on the basis of the model. A bias is added, as is an error term, the latter according to a Gaussian law.

Step 110: estimation of the observation vector on the basis of the state vector.

This entails estimating an observation vector, denoted $\hat{C}(t)$, on the basis of the state vector M(t). The estimation of the observation vector can be obtained by applying a matrix H, the so-called observation operator, to the state vector M(t), in the form of a matrix product. The matrix H makes it possible to spatially interpolate the measured data forming the observation vector C(t) so as to obtain, on the basis of the state vector, estimations $\hat{c}_p(t)$ of the nitrogen dioxide concentration at the level of each sensor $10_p$. The matrix H is of dimension $(N_p, N_m)$. With each row and with each column of the matrix H are respectively associated a sensor $10_p$ and a mesh cell $20_m$. The estimation of the observation vector $\hat{C}(t)$ is obtained according to the expression: $\hat{C}(t) = H \times M(t)$, (1) where x designates the matrix product.

The terms of the matrix H(p, m) depend on the relative position of a sensor $10_p$ with respect to the various mesh cells $20_m$. When the sensor $10_p$ coincides with the centre of a mesh cell $20_m$, the row H(p, .) of the matrix H corresponding to the sensor $10_p$ comprises only 0's, except at the level of the column corresponding to the mesh cell. In a general manner, the matrix is such that on a row H(p, .) corresponding to a sensor, the term of each column is all the higher when the column is associated with a mesh cell situated in proximity to the sensor. Preferably, the terms of the matrix H lie between 0 and 1.

Step 120: comparison between the observation vector C(t) and its estimation $\hat{C}(t)$ and calculation of a global bias.

In the course of this step, each term of the observation vector C(t) is compared with the term, corresponding to the same sensor $10_p$, of the estimation of the observation vector $\hat{C}(t)$ resulting from step 110. The comparison can take the form of a term-by-term subtraction or ratio.

On the basis of the comparison, a global bias $\varepsilon(t)$ is calculated, the bias representing, at the measurement instant t, a global comparison between the observation vector $C(t)$ and its estimation $\hat{C}(t)$. The global bias is a scalar quantity. It may, in particular, be determined on the basis of an average or of a median of a comparison, term by term, of the vectors $C(t)$ and $\hat{C}(t)$. For example, $$\varepsilon(t) = \frac{1}{N_p} \sum_{p=1}^{N_p} (C_p(t) - \hat{C}_p(t)), \quad (2)$$

where $C_p(t)$ and $\hat{C}_p(t)$ are respectively a term of rank p of the vectors $C(t)$ and $\hat{C}(t)$, corresponding to one and the same sensor $10_p$.

Step 130: debiasing of the state vector.

In the course of this step, the state vector $M(t)$ is corrected of the global bias $\varepsilon(t)$, by subtracting the global bias from each term of the state vector. A so-called debiased state vector denoted $M'(t)$ is then obtained.

Thus, $M'(t)=M(t)-E(t)$ (3) where $E(t)$ is a bias vector, of dimension $(N_m, 1)$, each term of which is equal to the global bias $\varepsilon(t)$. The term debiased signifies unbiased. The term debiasing signifies removal of the bias.

This step forms a first correction of the state vector, on the basis of a global bias calculated on the basis of the observations obtained by the sensors $10_p$. Such a bias may be due to emissions affecting the whole urban area under study, and originating, for example, from urban heating, or a diffuse pollution. The inventors have observed that taking a global bias such as this into account allowed an appreciable improvement in the precision of the state vector $M(t)$.

Figure 3A:
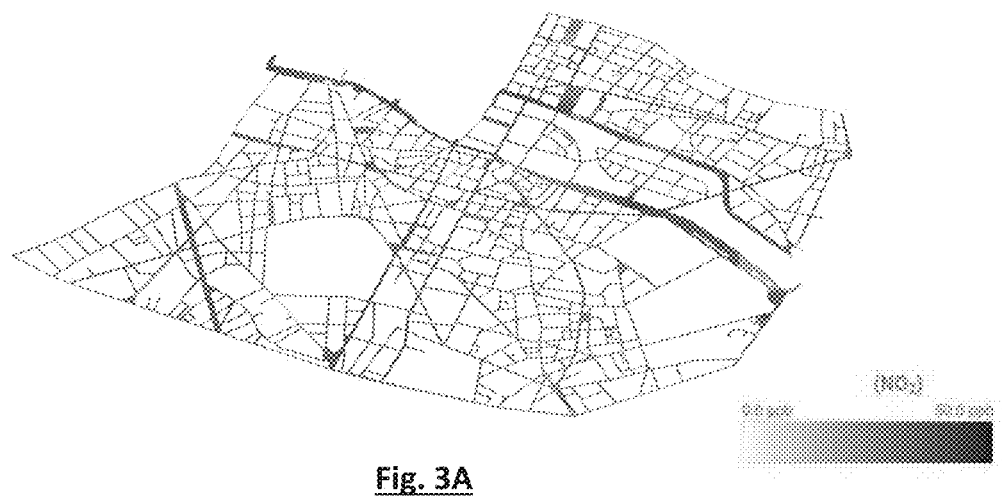
FIG. 3A represents the mapping of FIG. 1B after taking a global bias into account.

FIG. 3A shows a two-dimensional representation of the debiased state vector $M'(t)$. In this example, the value of the bias rises to 9.2 μg/m³. To each point of this figure there corresponds a mesh cell $20_m$ and a term of the $M'_m(t)$ debiased state vector.

Step 140: Debiased estimation of the observation vector.

In the course of step 140, the debiased state vector $M'(t)$, resulting from step 130, is fitted against the measurements arising from the sensors $10_p$. Accordingly, a so-called debiased estimation, denoted $\hat{C}'(t)$, of the observation vector is calculated by applying the observation operator H according to the expression $\hat{C}'(t)=H \times M'(t)$ (4), in a manner analogous to step 110.

Step 150: Fitting of the debiased state vector $M'(t)$ to the measurements.

In the course of step 150, a term-by-term comparison is performed between the debiased estimation of the observation vector $\hat{C}'(t)$, resulting from step 140, with the observation vector $C(t)$ established during step 100. The comparison can take the form of a subtraction or of a ratio. From this comparison is formed a local comparison vector comp(t). The local comparison vector comp(t) is of dimension $(N_p, 1)$. In contradistinction to the debiasing step (steps 120 and 130), the comparison is a vector quantity. Thus, each term $comp_p(t)$ of the local comparison vector is such that $comp_p(t)=\hat{C}'_p(t)-\hat{C}_p(t)$ (5), the index p representing the rank of each term, p lying between 1 and $N_p$. In contradistinction to the bias vector $E(t)$, the terms of the local comparison vector comp(t) may differ from one another, and are mutually independent.

Step 160: updating of the state vector.

After having formed the subject of a debiasing, during step 140, the state vector forms the subject of a second, so-called local, correction based on the local comparison vector comp(t) formed during step 150. A matrix, the so-called gain matrix K, makes it possible to perform a weighting of the correction to be made as a function of the distance of a mesh cell $20_m$ with respect to each sensor $10_p$. The gain matrix is of dimension $(N_m, N_p)$. With each row and with each column of the gain matrix are respectively associated a mesh cell $20_m$ and a sensor $10_p$. The terms of a row $K(m, .)$, corresponding to a mesh cell $20_m$, are all the higher the closer a sensor $10_p$, corresponding to a column, is to the mesh cell. The terms $K(m, p)$ of a gain matrix are preferably less than or equal to 1.

The updating of the state vector is performed according to the following expression:

$$M^*(t)=M(t)+K \times comp(t)=M(t)+K \times (C(t)-\hat{C}'(t)) \quad (6)$$

$$=M'(t)+K \times (C(t)-H \times M'(t)) \quad (6')$$

$M^*(t)$ corresponds to the updated state vector, making it possible to obtain a more realistic mapping of the pollutant.

This operation is equivalent to applying a local correction vector corr(t) to the debiased state vector $M'(t)$ so as to obtain a corrected (or updated) state vector $M^*(t)$. The local correction vector is of dimension $(N_p, 1)$ and corresponds to the application of the gain matrix to the local comparison vector comp(t), according to the expression:

$$corr(t)=K \times (C(t)-\hat{C}'(t))=K \times comp(t)=K \times (C(t)-H \times M'(t)) \quad (6'')$$

In contradistinction to the debiasing step, the local correction vector is not uniform.

Figure 3B:
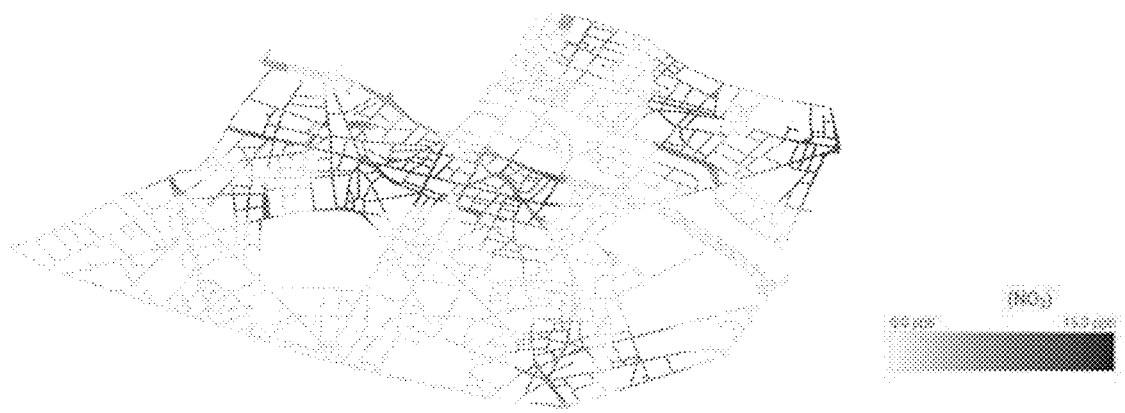
FIG. 3B shows a two-dimensional representation of the positive terms of a local correction vector.
Figure 3C:
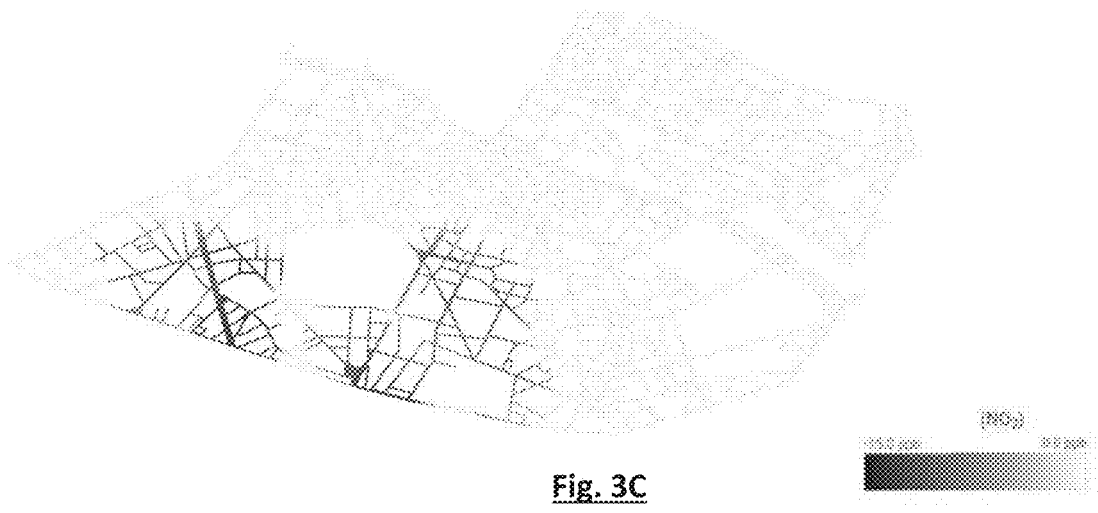
FIG. 3C shows a two-dimensional representation of the negative terms of a local correction vector.

In the course of this step, the correction of the state vector is not uniform, as during the debiasing, but differs from one term of the state vector to another. FIGS. 3B and 3C illustrate this aspect, and represent respectively the positive and negative terms of the correction vector corr(t) at the various mesh cells of the mapping. It is observed that the correction is local, the correction being more significant in certain parts than in others. It may be negative in certain parts, and positive in other parts.

The method makes it possible, through a sufficiently high density of sensors, to obtain a mapping taking account of local features of the traffic, for example, the occurrence of a bottleneck. The combination between the taking into account of a global bias, followed by a local correction step, makes it possible to improve the spatial resolution of the mapping arising from the updated state vector. In particular, it makes it possible to take account of local evolutions, affecting only a few mesh cells $20_m$. The mapping obtained is thus more reactive in regard to the occurrence of local features.

According to one embodiment, forming the subject of step 170 the updating of the state vector K is performed iteratively, by modifying the gain matrix at each iteration. Let n be the rank of each iteration and let $K_n$ be the gain matrix associated with each iteration, step 170 comprises an updating of the state vector resulting from step 160, or from a previous iteration n−1 in such a way that:

$$M_n^*(t)=M_{n-1}(t)+K_n \times comp_n(t) \quad (7)$$

With $comp_n(t)=C(t)-H \times M_{n-1}^*(t)$ (8), where:

$comp_n(t)$ is a comparison vector associated with the iteration of rank n;

$M_n^*(t)$ is the state vector updated in the course of the iteration of rank n;

C(t) is the previously defined measured observation vector; and

H is the previously defined observation operator.

Step 170 is repeated until an iteration criterion is attained. Such a criterion may be a predetermined number $N_n$ of iterations, or a sufficiently small disparity between two successive updates of the state vector $M_n^*(t)$, $M_{n+1}^*(t)$.

Each gain matrix $K_n$ can be determined in the course of each iteration n, as a function of a weight $w_{m,p}^n$ assigned to each iteration, the indices m and p representing respectively a row and a column of the gain matrix $K_n$. The weight is defined according to the following expression:

$$w_{m,p}^n = \frac{R_{n,p}^2 - r_{m,p}^2}{R_{n,p}^2 + r_{m,p}^2}, \text{ where:} \quad (9)$$

$R_{n,p}^2$ is a maximum radius of influence associated with each sensor $10_p$; for example, the radius of influence of a sensor disposed in the middle of a town square may be higher than the radius of influence of a sensor disposed in a narrow street; and $r_{m,p}$ is a distance between a sensor $10_p$ and a mesh cell $20_m$.

The value of each term $K_n(m, p)$ is then such that:

$$K_n(m, p) = 0 \text{ if } r_{m,p} > R_{n,p} \quad (10)$$

$$K_n(m, p) = \frac{w_{m,p}^n}{\left(\alpha^2 - \sum_p w_{m,p}^n\right)} \text{ if } r_{m,p} \leq R_{n,p}, \quad (11)$$

where:

$\alpha$ is a term representing an error between the observations and the model. $\alpha$ is a predefined scalar and may, for example, be equal to 0.1.

Thus, with each sensor $10_p$ is associated a neighbourhood $V_{n,p}$, whose extent depends on the maximum radius of influence $R_{n,p}$ associated with the sensor $10_p$. It is considered that the concentrations of the analyte in the mesh cells $20_m$ that are situated in this neighbourhood are impacted by the measurement arising from the sensor $10_p$. The more the iteration rank increases, the more the maximum radius of influence $R_{n,p}$ corresponding to one or more sensors $10_p$ decreases. For example, it is assumed that the maximum radius of influence is identical at each sensor $R_{n,p} = R_n$. During the first iteration (n=1), $R_{n=1}$ is fixed at 500 metres. During the second and third iterations $R_{n=2}$ and $R_{n=3}$ are fixed at 300 m and 100 m respectively.

According to a variant, the neighbourhood $V_{n,p}$ associated with a sensor $10_p$, that is to say the mesh cells $20_m$ at the level of which the concentration may be influenced by a measurement performed by the sensor, is not circular, but exhibits a predetermined shape, taking account of the topography, and, in particular, the presence of buildings around the sensor and/or of the dimensions of a street in which the sensor is placed. The neighbourhood of a sensor situated in a street may, for example, extend in a significant manner in a direction parallel to the axis of the street and in a lesser manner in a direction perpendicular to the axis of the street.

According to one embodiment, on the basis of an updated state vector, whether it be the state vector $M^*(t)$ updated during step 160 or a state vector $M_n^*(t)$ updated iteratively in the course of step 170, the method can comprise a step 200 of forecasting the state vector at a later instant t+dt following the measurement instant t. Accordingly, use is made of a state vector M(t+dt) provided by the model, in this instance the OSPM model. The time interval dt can be of the order of an hour. The state vector M(t+dt) can then be corrected using the state vector updated at the measurement instant t, according to the following expression:

$$M^*(t+dt) = (M(t+dt) - M(t)) + M_n^*(t) \quad (12), \text{ or}$$

$$M^*(t+dt) = (M(t+dt) - M(t)) + M^*(t) \quad (12')$$

Thus, the local correction performed on the model M(t+dt) depends on a variation between the state vectors at the respective measurement instants t and t+dt, and on the state vector updated at the measurement instant t, whether it be $M_n^*(t)$ or $M^*(t)$. It is observed that the correction of the later state vector does not require any new measurements, and is performed with respect to the state vector updated at the measurement instant.

Although described with regard to nitrogen dioxide, the present disclosure will be able to be implemented with other analytes, and, in particular, with polluting molecules or particles. Moreover, in the above example, the state vector established is of OSPM type, but other models known to the person skilled in the art may be applied to form the state vectors at each measurement instant.

The invention claimed is:

1. A method for estimating a mapping of a concentration of an analyte in an environment, using sensors distributed in the environment:

each sensor generating a measurement of an analyte concentration at various measurement instants, the measurements carried out by each sensor at each measurement instant forming an observation vector, each term of which corresponds to a measurement arising from a sensor of the sensors;

the environment being spatially meshed with a plurality of mesh cells, the analyte concentration at each mesh cell, at each measurement instant, forming a state vector, each term of which corresponding to an analyte concentration in a mesh cell;

the method comprising, using a processor:

a) obtaining a measured observation vector at a measurement instant, using the measurements performed by each sensor;

b) obtaining a state vector at the measurement instant and, using the state vector, estimating an observation vector at the measurement instant;

c) comparing the estimation of the observation vector, obtained in b), with the measured observation vector resulting from a), and, on the basis of the comparison, determining a global bias at the measurement instant, the global bias being a scalar representative of a comparison between several terms of the estimated observation vector and of the measured observation vector respectively, d) correcting the state vector obtained in b) with the global bias obtained in step c), so as to obtain a debiased state vector at the measurement instant;

e) on the basis of the debiased state vector obtained in d), obtaining a debiased estimation of observation vector at the measurement instant;

f) comparing the debiased estimation of the observation vector resulting from e) with the measured observation vector resulting from a), and, on the basis of the comparison, determining of a local correction vector; and g) updating the state vector at the measurement instant, the latter being replaced with a sum of the debiased state vector resulting from d) and the local correction vector resulting from f), the updating of the state vector making it possible to estimate the mapping of the concentration of the analyte in various mesh cells.

2. The method according to claim 1, wherein b), the observation vector is estimated by applying an observation matrix to the state vector.

3. The method according to claim 1, wherein c) comprises:
 ci) establishing comparisons between various terms of the observation vector estimated in b) and of the observation vector measured in a);
 cii) calculating an average or median value of each comparison resulting from ci); and
 ciii) obtaining the global bias on the basis of an average or a median value resulting from cii).

4. The method according to claim 1, wherein d) comprises subtracting of the global bias from each term of the state vector.

5. The method according to claim 1, wherein in e), the debiased estimation of the observation vector is obtained by applying an observation matrix to the debiased state vector.

6. The method according to claim 1, wherein f) comprises:
 fi) establishing a comparison vector, resulting from a comparison, term by term, between the observation vector resulting from a) and the debiased estimation of the observation vector resulting from e);
 fii) taking into account of a gain matrix; and
 fiii) applying the gain matrix to the comparison vector so as to form the correction vector.

7. The method according to claim 2, wherein, following g), the method further comprises:
 h) iteratively updating the state vector, each iteration being associated to an iteration rank, the method further comprising:
  hi) taking into account a gain matrix corresponding to the iteration rank;
  hii) determining a comparison vector, associated with the iteration rank, by comparing the observation vector resulting from a) with a vector resulting from the application of the observation matrix to the state vector resulting from g), or to the state vector resulting from a previous iteration;
  hiii) applying the gain matrix of hi) to the comparison vector determined in hii), so as to obtain a local correction vector associated with the iteration rank;
  hiv) updating the state vector, the latter being replaced with a sum of the state vector resulting from g), or from a previous iteration, with the local correction vector resulting from hiii); and
  hv) repeating hi) to hiv) or stopping of the iteration.

8. The method according to claim 6, wherein each term of the gain matrix is associated with a mesh cell and with a sensor, a value of the term being all the higher the closer the mesh cell is to the sensor.

9. The method according to claim 7, wherein each term of the gain matrix is associated with a mesh cell and with a sensor, a value of the term being all the higher the closer the mesh cell is to the sensor.

10. The method according to claim 1, wherein b) comprises forming the state vector by using a model established on the basis of data relating to the road traffic in the environment, of the topography of the environment as well as of meteorological data relating to the environment, the model resulting in a concentration of the analyte at the level within each mesh cell.

11. The method according to claim 1, further comprising:
 taking into account of a later state vector with respect to a later instant following the measurement instant; and
 correcting the later state vector as a function of the state vector updated, at the measurement instant, during g).

12. The method according to claim 7, comprising the following steps:
 taking into account of a later state vector with respect to a later instant following the measurement instant; and
 correcting the later state vector as a function of the state vector updated, at the measurement instant, during step h).

13. The method according to claim 2, wherein each term of the observation matrix is associated with a mesh cell and with a sensor, a value of the term being all the higher the closer the mesh cell is to the sensor.

14. The method according to claim 5, wherein each term of the observation matrix is associated with a mesh cell and with a sensor, a value of the term being all the higher the closer the mesh cell is to the sensor.

15. The method according to claim 7, wherein each term of an observation matrix is associated with a mesh cell and with a sensor, a value of the term being all the higher the closer the mesh cell is to the sensor.

* * * * *